United States Patent
Stella et al.

(10) Patent No.: US 9,101,551 B2
(45) Date of Patent: Aug. 11, 2015

(54) PERSONAL CLEANSING COMPOSITIONS AND METHODS

(71) Applicant: The Procter & Gamble Company, Cincinnati, OH (US)

(72) Inventors: Qing Stella, Cincinnati, OH (US); Gerald John Guskey, Symmes Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 14/049,897

(22) Filed: Oct. 9, 2013

(65) Prior Publication Data

US 2015/0096582 A1    Apr. 9, 2015

(51) Int. Cl.
| | |
|---|---|
| *A61Q 19/10* | (2006.01) |
| *A61Q 5/02* | (2006.01) |
| *A61K 8/81* | (2006.01) |
| *A61K 8/46* | (2006.01) |
| *A61K 8/42* | (2006.01) |
| *A61K 8/20* | (2006.01) |
| *A61K 8/34* | (2006.01) |
| *A61K 8/41* | (2006.01) |
| *A61K 8/97* | (2006.01) |
| *A61Q 5/12* | (2006.01) |

(52) U.S. Cl.
CPC ............... *A61K 8/8152* (2013.01); *A61K 8/20* (2013.01); *A61K 8/342* (2013.01); *A61K 8/416* (2013.01); *A61K 8/42* (2013.01); *A61K 8/463* (2013.01); *A61K 8/97* (2013.01); *A61Q 5/02* (2013.01); *A61Q 5/12* (2013.01); *A61Q 19/10* (2013.01)

(58) Field of Classification Search
None
See application file for complete search history.

(56) References Cited

U.S. PATENT DOCUMENTS

| | | | |
|---|---|---|---|
| 3,711,435 A | 1/1973 | Hammer et al. | |
| 3,954,113 A * | 5/1976 | Bohrer et al. | 132/200 |
| 4,879,114 A | 11/1989 | Catsimpoolas et al. | |
| 5,064,879 A | 11/1991 | Shiga et al. | |
| 5,115,036 A | 5/1992 | Shiga et al. | |
| 5,208,016 A | 5/1993 | Ohmae et al. | |
| 6,932,964 B1 | 8/2005 | Kim et al. | |
| 7,531,497 B2 | 5/2009 | Midha et al. | |
| 7,867,962 B2 | 1/2011 | Wei et al. | |
| 7,888,306 B2 | 2/2011 | SenGupta et al. | |
| 8,084,408 B2 | 12/2011 | Wei et al. | |
| 8,093,192 B2 | 1/2012 | Liu et al. | |
| 8,303,943 B2 | 11/2012 | Kim et al. | |
| 2006/0079419 A1 | 4/2006 | Wagner et al. | |
| 2006/0079420 A1 | 4/2006 | Wagner et al. | |
| 2006/0079421 A1 | 4/2006 | Wagner et al. | |
| 2007/0280976 A1 | 12/2007 | Taylor et al. | |
| 2008/0210561 A1 | 9/2008 | Mahler | |
| 2009/0107062 A1 | 4/2009 | Pedersen | |
| 2009/0220443 A1 | 9/2009 | Braksmayer et al. | |
| 2010/0119468 A1 | 5/2010 | Garcia Castro et al. | |
| 2010/0184847 A1 | 7/2010 | Shin et al. | |
| 2011/0045039 A1 | 2/2011 | Sunkel et al. | |
| 2011/0247954 A1 | 10/2011 | Wei | |
| 2011/0250141 A1 | 10/2011 | Wei | |
| 2011/0251872 A1 | 10/2011 | Wei | |
| 2011/0253157 A1 | 10/2011 | Wei | |
| 2011/0253158 A1 | 10/2011 | Wei | |
| 2011/0257020 A1 | 10/2011 | Stella et al. | |
| 2011/0257030 A1 | 10/2011 | Stella et al. | |
| 2012/0015009 A9 | 1/2012 | Taylor et al. | |
| 2012/0184448 A1 | 7/2012 | Stella et al. | |
| 2012/0282309 A1 | 11/2012 | Dihora et al. | |
| 2013/0280174 A1 | 10/2013 | Lipic et al. | |
| 2013/0280192 A1 | 10/2013 | Carter et al. | |
| 2013/0280193 A1 | 10/2013 | Carter et al. | |
| 2013/0280202 A1 | 10/2013 | Stella et al. | |
| 2013/0280356 A1 | 10/2013 | Stella et al. | |
| 2013/0281551 A1 | 10/2013 | Stella et al. | |
| 2014/0023606 A1 | 1/2014 | Scheunemann et al. | |
| 2014/0057997 A1 | 2/2014 | Chevalier et al. | |

FOREIGN PATENT DOCUMENTS

| | | |
|---|---|---|
| EP | 2505180 | 10/2012 |
| GB | 1284489 | 8/1972 |
| JP | 06262060 | 9/1994 |
| JP | 2009126791 | 6/2009 |
| JP | 2010235567 | 10/2010 |
| JP | 2011178667 | 9/2011 |
| WO | 2011/117345 A1 | 9/2011 |
| WO | 2012/075293 A2 | 6/2012 |

OTHER PUBLICATIONS

International Search Report PCT/US2014/059627 including the Written Opinion of the International Searching Authority dated Jan. 5, 2015, 12 pages.
U.S. Appl. No. 14/245,254, filed Apr. 4, 2014, Carter et al.
U.S. Appl. No. 14/245,276, filed Apr. 4, 2014, Carter et al.
U.S. Appl. No. 14/049,938, filed Oct. 9, 2013, Stella et al.

* cited by examiner

*Primary Examiner* — Jyothsna Venkat

(57) ABSTRACT

A personal care composition includes a surfactant, a water soluble cationic polymer, a hydrophobic benefit agent, and a hydrophobic cationic polyethylene polymer.

3 Claims, 3 Drawing Sheets

PERSONAL CLEANSING COMPOSITIONS AND METHODS

TECHNICAL FIELD

The present disclosure generally relates to personal cleansing compositions and methods of enhancing deposition of hydrophobic benefit agents.

BACKGROUND OF THE INVENTION

Over time, skin cleansing has become part of a personal hygiene regimen. The cleansing of the skin allows for the removal of dirt, debris, bacteria, and a myriad of other things that can cause harm to the skin or the body. Cleansing is often done with the aid of a surfactant. The surfactant works to help remove deposited materials from the skin. Unfortunately, surfactants can also act to remove good things from the skin as well, like oil. The oil on the skin helps, for example, to protect the skin from losing too much moisture. Removal of too much oil can leave the skin vulnerable to becoming dry. One solution for this problem is to utilize a milder surfactant. Another solution is to replace what is removed by depositing a replacement material on the skin. Historically, however, there has been a struggle to effectively deposit these replacement materials on the skin, especially in rinse off products like cleansers. As such, there is a need for personal care compositions that provide enhanced deposition of materials on the skin.

SUMMARY OF THE INVENTION

A personal care composition comprises a cleansing phase comprising a surfactant and a water soluble cationic polymer, and a benefit phase comprising a hydrophobic benefit agent and a cationic hydrophobic polyethylene polymer, wherein the composition has a pH from about 4.5 to about 9.

A personal cleansing composition comprises a surfactant, guar hydroxypropyltrimonium chloride, a hydrophobic benefit agent, and a cationic hydrophobic polyethylene polymer.

A personal cleansing composition, comprising: up to about 95% by weight of the composition of a cleansing phase comprising an anionic surfactant, a co-surfactant, and guar hydroxypropyltrimonium chloride; and about 20% or less by weight of the composition of a benefit phase comprising a hydrophobic benefit agent and poly(ethylene-co-DMAEMA), wherein the poly(ethylene-co-DMAEMA becomes cationic upon combining the cleansing phase and benefit phase and the composition has a pH from about 4.5 to about 9.0.

These and other combinations will be understood from the more detailed description below.

DETAILED DESCRIPTION

I. Definitions

Figure 1:
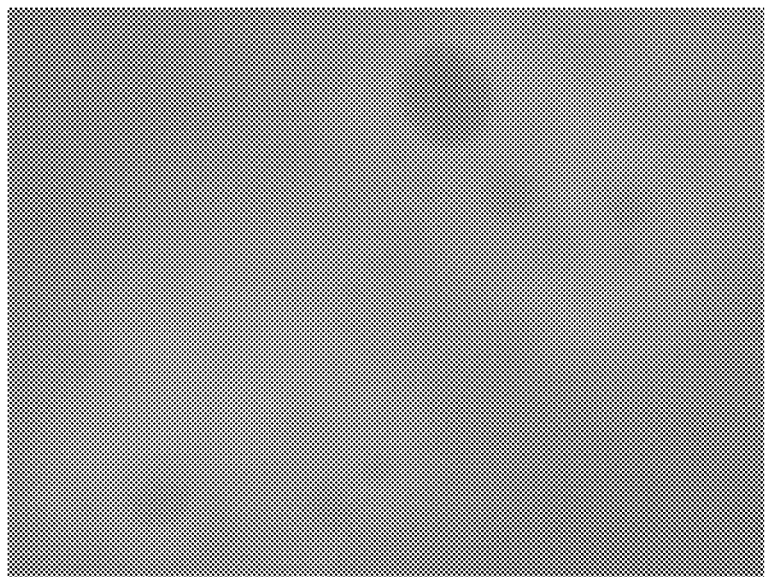
FIG. 1 is a picture of a micrograph showing fluorescently tagged amino functionality of a cationic polymer in a coacervate.

As used herein, the following terms shall have the meaning specified thereafter:

"About" as defined herein accounts for +/−10% of the specified number.

"Anhydrous" refers to those compositions, and components thereof, which are substantially free of water.

"DMAEMA" refers to dimethylaminoethyl methacrylate.

"Multiphase" refers to compositions comprising at least two phases which can be chemically distinct (e.g. a cleansing phase and a benefit phase). Such phases can be in direct physical contact with one another. A personal care composition can be a multiphase personal care composition where phases of the personal care composition can be blended or mixed to a significant degree, but still be physically distinct. In these situations, the physical distinctiveness is undetectable to the naked eye. The personal care composition can also be a multiphase personal care composition where the phases are in physical contact and are visually distinct. Visually distinct phases can take many forms, for example, they can appear as striped, marbled, etc.

"Package" refers to any suitable container for a personal care composition including but not limited to a bottle, tottle, tube, jar, non-aerosol pump, box, wrapper, and combinations thereof.

"Personal care composition" refers to compositions intended for topical application to skin and/or hair. Personal care compositions can be rinse-off formulations, in which the product can be applied topically to the skin and/or hair and then subsequently rinsed within seconds to minutes from the skin or hair with water. The product could also be wiped off using a substrate. The personal care compositions can also be used as shaving aids. The personal care compositions can be extrudable or dispensable from a package. Examples of personal care compositions can include but are not limited to bar soap, shampoo, conditioning shampoo, body wash, moisturizing body wash, shower gels, skin cleansers, cleansing milks, in shower body moisturizer, pet shampoo, shaving preparations, and cleansing compositions used in conjunction with a disposable cleansing cloth.

"SLS" refers to sodium lauryl sulfate.

"STnS" refers to sodium trideceth(n) sulfate, wherein n can define the average number of moles of ethoxylate per molecule.

The phrase "substantially free of" as used herein, unless otherwise specified means that the personal care composition comprises less than about 5%, less than about 3%, less than about 1%, or even less than about 0.1% of the stated ingredient. The term "free of" as used herein means that the personal care composition comprises 0% of the stated ingredient that is the ingredient has not been added to the personal care composition. However, these ingredients may incidentally form as a byproduct or a reaction product of the other components of the personal care composition.

The devices, apparatuses, methods, components, and/or compositions of the present invention can include, consist essentially of, or consist of, the components of the present invention as well as other ingredients described herein. As used herein, "consisting essentially of" means that the devices, apparatuses, methods, components, and/or compositions may include additional ingredients, but only if the additional ingredients do not materially alter the basic and novel characteristics of the claimed devices, apparatuses, methods, components, and/or compositions.

All percentages and ratios used herein are by weight of the total composition and all measurements made are at 25° C., unless otherwise designated.

II. Personal Cleansing Compositions

As discussed above, personal cleansing compositions are often used to remove dirt or debris from the skin or hair. In addition to the dirt and debris, oil (also known as sebum) is also removed through the cleansing process. While too much sebum on the skin or hair is unwanted and there is a need to remove sebum to prevent its build-up on the skin, a certain amount of sebum is good for the skin and hair as it helps protect them. Sebum can act like a barrier holding moisture into the skin and hair so that it doesn't become overly dry.

Not only do we remove sebum through the cleansing process, but sometimes individuals do not produce enough sebum from the start and thus are plagued with dry skin and hair issues. These types of issues also arise with the change in the weather as different seasons have different humidity levels. For example, there is a tendency for the winter months to be more dry and thus for there to be a higher number of people with dry skin and/or hair during that time of year.

While the use of milder surfactants can lessen the impact to the sebum, there is still a desire to deposit hydrophobic benefit agents onto the skin to help further decrease the impact of sebum removal and to especially help those people who may have already had dry skin or hair to start. Depositing benefit agents onto the skin during a process which is set-up to remove things from the skin has always proved a challenge.

One way to help improve the deposition of benefit agents is through the use of coacervates. Coacervation is the chemical process of encapsulation. For personal cleansing compositions, the coacervation often takes place during the rinsing process as the addition of water (i.e. dilution) of the personal cleansing compositions initiates the changes in hydrophobic and electrostatic interactions which trigger the formation of coacervates. Based on the chemistry of the system, it is believed the coacervates encapsulate the benefit agent as they are formed. This encapsulation results in the benefit agent having a larger particle size and improved visco-elasticity, both of which are believed to help improve the deposition of the benefit agent onto skin or hair.

One material used to help encourage the formation of coacervates upon dilution of a personal cleansing composition is a water soluble cationic polymer. For example, looking at Example 1 below, personal cleansing composition Formulation A contains a benefit agent (soy bean oil) and no water soluble cationic polymer. It has an in vitro deposition of 2.0 $\mu g/cm^2$ measured per the Fast Mice Method given in detail below. Comparing that to Formulation E which with the addition of a water soluble cationic polymer (guar hydroxypropyltrimonium chloride) increases the in vitro deposition to 16 $\mu g/cm^2$.

Another material considered for deposition enhancement is hydrophobic cationic polyethylene polymers. However, if you look at personal cleansing composition Formulations B-D in Example 1 below, you see that utilizing a hydrophobic cationic polyethylene polymer resulted in, in vitro depositions of 2.7, 2.2, and 2.6 $\mu g/cm^2$ respectively. Thus, there is only a negligible increase over the deposition seen without any cationic polymer as discussed above for Formulation A.

Surprisingly, the present inventors discovered the addition of a cationic hydrophobic polymer to personal cleansing compositions comprising a water soluble cationic polymer dramatically improved deposition. Inventive formulations F-H in Example 1 below showed in vitro deposition of 55, 177, and 392 $\mu g/cm^2$ respectively. Thus, the deposition of the benefit agent increased 20 fold in one instance and by several fold at the minimum.

Without being limited by theory, it is believed the increased deposition from the water soluble cationic polymer and hydrophobic cationic polyethylene polymer combination at least partially results from an enhanced encapsulation of the benefit agent in the coacervate. This is illustrated in FIG. 1 which is a picture of a micrograph where the amino functionality of a cationic hydrophobic polymer (here, poly(ethylene-co-DMAEMA) is fluorescently tagged.

As seen in FIG. 1, the polymer (fluoresced, bright circle) resides at the interface of the benefit agent (which is dark) and the coacervate. It is believed at least part of the hydrophobic portions of the water soluble cationic hydrophobic polyethylene polymer reside inside the hydrophobic benefit agent while the cationic portions of the cationic hydrophobic polyethylene polymer tend to migrate to the interface of the hydrophobic benefit agent and the coacervate. The integration of the cationic portion of the hydrophobic polymer into the benefit agent allows for an interaction of the agent itself with, for example, an anionic surfactant to more strongly integrate the benefit agent into the coacervate.

The stronger interactions between the benefit agent and coacervate are at least partially contributed to the cationic charges and the charge mobility on the hydrophobic polyethylene polymer. In addition to anionic surfactant absorption on the surface of the benefit agent through hydrophobic interaction, the cationic hydrophobic polyethylene polymer provides additional cationic charges that form ion pairs with anionic surfactant through electrostatic interaction. Furthermore, the charge mobility is substantially increased as they are attached to a polymer chain. The higher mobility of the ion pairs enhances the ability of the benefit agent to integrate into a coacervate. The anionic surfactant both absorbed on the surface of the benefit agent and ion paired with the cationic hydrophobic polyethylene polymer facilitate the integration of the benefit agent into a coacervate. This is in contrast to when only a water soluble cationic polymer is present, only the electrostatic interactions of the water soluble cationic polymer and the anionic surfactant absorbed on the surface of benefit agent droplets are helping hold the benefit agent in the coacervate.

Figure 2:
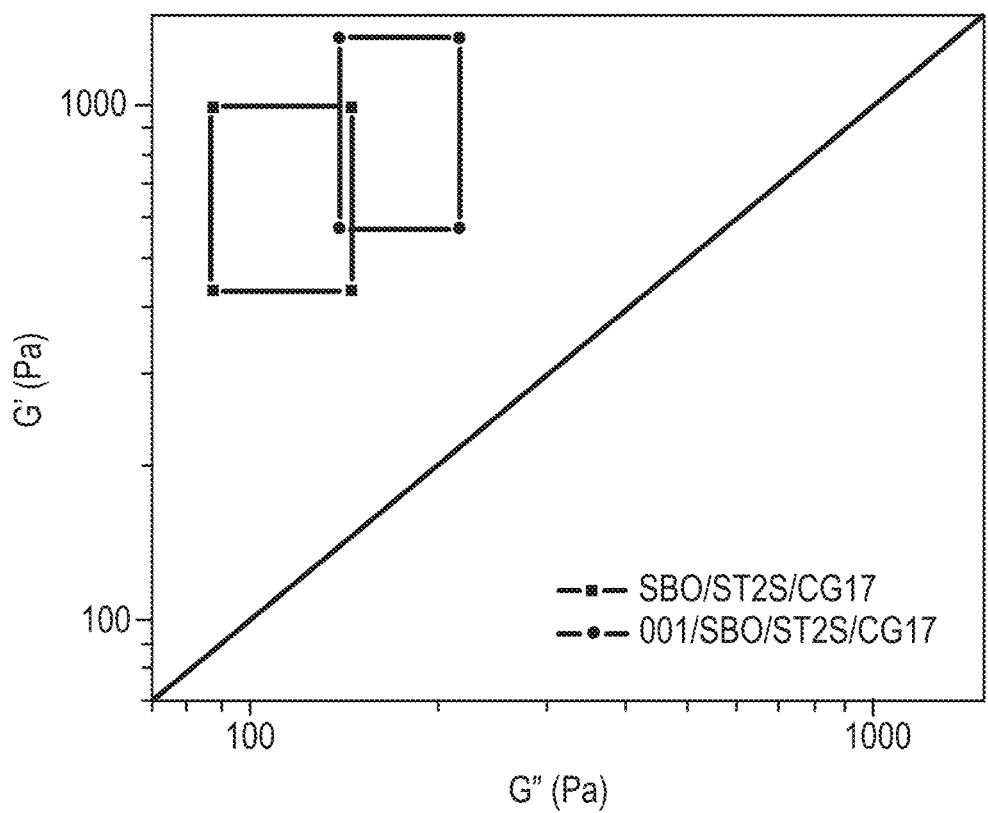
FIG. 2 is a graph showing the rheology of coacervate-soybean oil-Polymer 1 complex compared to the rheology of coacervate-soybean oil complex.

Further, without being limited by theory, it is also believed the combination of hydrophobic polyethylene and water soluble cationic polymers in a personal cleansing composition and the interactions discussed above also result in the enhancement of the benefit agent coacervate rheology modulus. Coacervate rheology attributes to the deposition of an entrapped benefit agent. Deposition enhancing coacervates typically are viscoelastic. Appropriate viscosity of the coacervate-benefit agent complex, measured by loss modulus (G"), provides fluidity and spreading when product is applied to the skin surface under shear. The elasticity, measured by storage modulus (G'), provides rigidity for the complex to resist removal forces, like water rinsing, to retain the complex on the skin or hair. A good balance of G' and G" is desired for improved deposition. This is exemplified in FIG. 2 which shows the rheology of a coacervate-soybean oil-Polymer 1 complex compared to the rheology of a coacervate-soybean oil complex.

Not only was a difference in deposition discovered with the addition of a cationic hydrophobic polyethylene polymer, but it has also been discovered that properties of the hydrophobic polyethylene polymer itself further influence deposition, as illustrated in the chart below.

| Polymer (poly(ethylene-co-DMAEMA)) | Formulation used from Example 1 | % DMAEMA (amino monomer) (by weight of the cationic hydrophobic polymer) | Viscosity (cps) at 120° C. | Deposition (μg/cm²) |
|---|---|---|---|---|
| Polymer 6 | F | 49% | 150 | 55 |
| Polymer 4 | G | 34% | 160 | 177 |
| Polymer 1 | H | 37% | 3600 | 392 |

As can be seen from this chart, cationic hydrophobic polyethylene polymers 6 and 4 have a similar viscosity, but a dissimilar percentage of amino monomer. This difference in the amino monomer appears to affect the deposition of the benefit agent as the formulation containing polymer 6 deposited only 55 μg/cm² and the formulations containing polymer 4 deposited 177 g/cm². Thus, it appears a lower % of amino monomer in the polymer will give more effective deposition of the benefit agent.

As can also be seen from the chart, cationic hydrophobic polymers 4 and 1 have a similar percentage of amino monomer, but a dissimilar viscosity. This difference in the viscosity appears to affect the deposition of the benefit agent as the formulation containing polymer 4 deposited only 177 μg/cm² and the formulation containing polymer 1 deposited 392 μg/cm². Thus, it appears a higher viscosity in the polymer will also give more effective deposition of the benefit agent.

Figure 3:
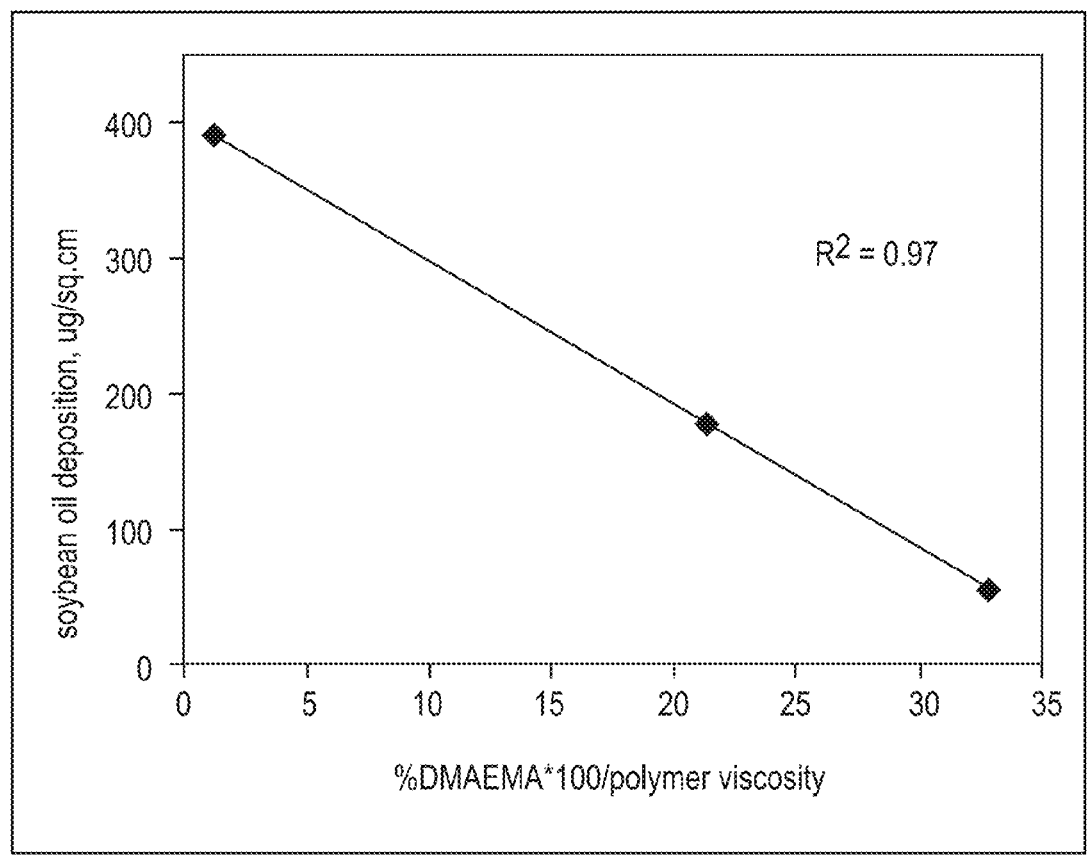
FIG. 3 is a graph showing a relationship between the ratio of the % amino monomer and the viscosity of the polymer, and deposition.

As shown in FIG. 3, it also appears a ratio of the % amino monomer and the viscosity of the polymer could also be predictive of deposition. Deposition, which we have exemplified with soy bean oil as the benefit agent, appears to have a reciprocal linear relationship with the ratio of % amino monomer*100/polymer viscosity at 120° C., indicating a balanced combination of polymer chain length and % amino monomer gives deposition optimization. For example, the ratio for polymer 1 is 1, polymer 4 is 21, and for polymer 6 is 33. A lower % amino monomer and higher polymer viscosity can be preferred. The ratio of % amino monomer to polymer viscosity can be, for example, from 0.1 to 50.

Personal cleansing compositions can be multi-phase or single phase. While the components for personal cleansing compositions will be discussed below as being multi-phase for simplicity, the components for each phase could also be used in a single phase. A personal cleansing composition can comprise a cleansing phase and a benefit phase. The cleaning phase and the benefit phase can be blended. The cleaning phase and the benefit phase can also be patterned (e.g. striped and/or marbled).

A. CLEANSING PHASE

A cleansing phase can include a surfactant. The personal care composition can further comprise from about 0.1% to 20%, by weight of the rinse-off personal care composition, of a surfactant. Surfactants can comprise anionic surfactants, nonionic surfactants, amphoteric surfactants, zwitterionic surfactants, cationic surfactants, or mixtures thereof. The personal care composition can include at least one anionic surfactant. A personal care composition can also comprise, for example, an anionic surfactant, amphoteric surfactant, and a zwitterionic surfactant. Suitable amphoteric or zwitterionic surfactants, for example, can include those described in U.S. Pat. No. 5,104,646 and U.S. Pat. No. 5,106,609.

Anionic surfactants suitable for use in the cleansing phase of the present compositions include alkyl and alkyl ether sulfates. These materials have the respective formula $ROSO_3M$ and $RO(C_2H_4O)_xSO_3M$, wherein R is alkyl or alkenyl of from about 8 to about 24 carbon atoms, wherein x is about 1 to about 10, and M is a water-soluble cation such as ammonium, sodium, potassium, or triethanolamine. The alkyl ether sulfates are typically made as condensation products of ethylene oxide and monohydric alcohols having from about 8 to about 24 carbon atoms. R may have from about 10 to about 18 carbon atoms in both the alkyl and alkyl ether sulfates. The alcohols can be derived from fats, e.g., coconut oil or tallow, or can be synthetic. Lauryl alcohol and straight chain alcohols derived from coconut oil may be used. Such alcohols may be reacted with about 1 or about 3 to about 10 or about 5 molar proportions of ethylene oxide. The resulting mixture of molecular species may have, for example, an average of 3 moles of ethylene oxide per mole of alcohol, is sulfated and neutralized.

Specific examples of alkyl ether sulfates which may be used in the cleansing phase are sodium and ammonium salts of coconut alkyl triethylene glycol ether sulfate; tallow alkyl triethylene glycol ether sulfate, and tallow alkyl hexaoxyethylene sulfate. Suitable alkyl ether sulfates are those comprising a mixture of individual compounds, said mixture having an average alkyl chain length of from about 10 to about 16 carbon atoms and an average degree of ethoxylation of from about 1 to about 4 moles of ethylene oxide.

Other suitable anionic surfactants include water-soluble salts of the organic, sulfuric acid reaction products of the general formula [$R^1$—$SO_3$-M], wherein $R^1$ is chosen from the group consisting of a straight or branched chain, saturated aliphatic hydrocarbon radical having from about 8 to about 24, or about 10 to about 18, carbon atoms; and M is a cation. Suitable examples are the salts of an organic sulfuric acid reaction product of a hydrocarbon of the methane series, including iso-, neo-, ineso-, and n-paraffins, having about 8 to about 24 carbon atoms, preferably about 10 to about 18 carbon atoms and a sulfonating agent, e.g., $SO_3$, $H_2SO_4$, oleum, obtained according to known sulfonation methods, including bleaching and hydrolysis. Preferred are alkali metal and ammonium sulfonated $C_{10-18}$ n-paraffins.

Suitable anionic surfactants for use in the cleansing phase include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, monoethanolamine cocoyl sulfate, sodium tridecyl benzene sulfonate, sodium dodecyl benzene sulfonate, and combinations thereof.

Anionic surfactants with branched alkyl chains such as sodium trideceth sulfate, for example, may be employed. Mixtures of anionic surfactants can also be used.

Amphoteric surfactants can include those that can be broadly described as derivatives of aliphatic secondary and tertiary amines in which an aliphatic radical can be straight or branched chain and wherein an aliphatic substituent can contain from about 8 to about 18 carbon atoms such that one carbon atom can contain an anionic water solubilizing group, e.g., carboxy, sulfonate, sulfate, phosphate, or phosphonate. Examples of compounds falling within this definition can be sodium 3-dodecyl-aminopropionate, sodium 3-dodecylaminopropane sulfonate, sodium lauryl sarcosinate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and products described in U.S. Pat. No. 2,528,378. Other examples of amphoteric surfactants can include sodium lauroamphoacetate, sodium cocoamphoactetate, disodium lauroamphoacetate disodium cocodiamphoacetate, and mixtures thereof. Amphoacetates and diamphoacetates can also be used.

Zwitterionic surfactants suitable for use as cleansing surfactant in the structured aqueous cleansing phase include those that are broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate.

Other zwitterionic surfactants suitable for use in the cleansing phase include betaines, including high alkyl betaines such as coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gammacarboxypropyl betaine, and lauryl bis-(2-hydroxypropyl)alphacarboxyethyl betaine. The sulfobetaines may be represented by coco dimethyl sulfopropyl betaine, stearyl dimethyl sulfopropyl betaine, lauryl dimethyl sulfoethyl betaine, lauryl bis-(2-hydroxyethyl) sulfopropyl betaine and the like; amidobetaines and amidosulfobetaines, wherein the $RCONH(CH_2)_3$ radical is attached to the nitrogen atom of the betaine are also useful in the present compositions.

Amphoacetates and diamphoacetates can also be used. Non-limiting examples of suitable amphoacetates and diamphoacetates include sodium lauroamphoacetate, sodium cocoamphoactetate, disodium lauroamphoacetate, and disodium cocodiamphoacetate.

Cationic surfactants can also be used in the cleansing phase and may represent less than about 5%, by weight of the cleansing phase.

Suitable nonionic surfactants for use in structured aqueous cleansing phase include condensation products of alkylene oxide groups (hydrophilic in nature) with an organic hydrophobic compound, which may be aliphatic or alkyl aromatic in nature.

Other suitable surfactants or cosurfactants that can generally be used in a cleansing phase for a rinse-off personal care composition are described in McCutcheon's: Detergents and Emulsifiers North American Edition (Allured Publishing Corporation 1947) (1986), McCutcheon's, Functional Materials North American Edition (Allured Publishing Corporation 1973) (1992) and U.S. Pat. No. 3,929,678 (filed Aug. 1, 1974).

The cleansing phase can include a structuring surfactant. Such a structuring surfactant can be included from about 1% to about 20%, by weight of the personal care composition; from about 2% to about 15%, by weight of the personal care composition; or from about 5% to about 10%, by weight of the personal care composition. Such a structuring surfactant can include sodium trideceth(n) sulfate, hereinafter STnS, wherein n defines the average moles of ethoxylation. n can range, for example, from about 0 to about 3; n can range from about 0.5 to about 2.7; from about 1.1 to about 2.5; from about 1.8 to about 2.2; or n can be about 2. When n is less than 3, STnS can provide improved stability, improved compatibility of benefit agents within the rinse-off personal care compositions, and/or increased mildness of the rinse-off personal care compositions, such described benefits of STnS are disclosed in U.S. Patent Application Pub. No. 2012/0009285.

The personal care composition can further comprise from about 0.1% to 20%, by weight of the personal care composition, of a cosurfactant. Cosurfactants can comprise amphoteric surfactants, zwitterionic surfactants, or mixtures thereof. Examples of these types of surfactant are discussed above.

The personal care composition can also comprise a water soluble cationic polymer. The water soluble cationic polymer can be present from about 0.001 to about 3 percent by weight of the personal care composition. The water soluble cationic polymer can also be present from about 0.05 to about 2 percent by weight of the personal care composition. The water soluble cationic polymer can also be present from about 0.1 to about 1 by weight of the personal care composition. The polymer may be in one or more phases as a deposition aid for the benefit agents described herein. Suitable cationic deposition polymers for use in the compositions of the present invention contain, for example, cationic nitrogen-containing moieties such as quaternary ammonium or cationic protonated amino moieties. The cationic protonated amines can be primary, secondary, or tertiary amines depending upon the particular species and the selected pH of the personal care composition.

Nonlimiting examples of cationic deposition polymers for use in compositions include polysaccharide polymers, such as cationic cellulose derivatives. The cationic cellulose polymers can be, for example, the salts of hydroxyethyl cellulose reacted with trimethyl ammonium substituted epoxide, referred to in the industry (CTFA) as Polyquaternium 10 which are available from Amerchol Corp. (Edison, N.J., USA) in their Polymer KG, JR and LR series of polymers. The water soluble cationic polymer comprises, for example, KG-30M. Other suitable cationic deposition polymers include cationic guar gum derivatives, such as guar hydroxypropyltrimonium chloride, specific examples of which include the Jaguar series (preferably Jaguar C-17) commercially available from Rhodia Inc., and N-Hance polymer series commercially available from Ashland.

The water soluble cationic polymer can comprise, for example, a cationic guar. In one example, the cationic guar comprises guar hydroxypropyltrimonium chloride. The guar hydroxypropyltrimonium chloride can comprise, for example, N-hance™ CG-17 Cationic Guar. The cationic guar can be, for example, selected from a group consisting of N-hance™ 3196, Jaguar C-500, Jaguar C-17, and a combination thereof.

The water soluble cationic polymer can also comprise synthetic polyacrylamides. Examples of suitable synthetic polyacrylamides include polyquaternium 76 and Polymethylenebis-acrylamide methacrylamido propyltrimethyl ammonium chloride (PAMMAPTAC, AM:MAPTAC ratio 88:12. In one example, the water soluble cationic polymer comprises PAM/MAPTAC.

A cleansing phase of a personal care composition can also include an associative polymer. Such associative polymer can be a crosslinked, alkali swellable, associative polymer comprising acidic monomers and associative monomers with hydrophobic end groups, whereby the associative polymer comprises a percentage hydrophobic modification and a hydrophobic side chain comprising alkyl functional groups. Without intending to be limited by theory, it is believed the acidic monomers can contribute to an ability of the associative polymer to swell in water upon neutralization of acidic groups; and associative monomers anchor the associative polymer into structured surfactant hydrophobic domains, e.g., lamellae, to confer structure to the surfactant phase and keep the associative polymer from collapsing and losing effectiveness in a presence of an electrolyte.

The crosslinked, associative polymer can comprise a percentage hydrophobic modification, which is a mole percentage of monomers expressed as a percentage of a total number of all monomers in a polymer backbone, including both acidic and other non-acidic monomers. Percentage hydrophobic modification of the associative polymer, hereafter % HM, can be determined by the ratio of monomers added during synthesis, or by analytical techniques such as proton nuclear magnetic resonance (NMR). Associative alkyl side chains can comprise, for example, butyl, propyl, stearyl, steareth, cetyl, lauryl, laureth, octyl, behenyl, beheneth, steareth, or other linear, branched, saturated, or unsaturated alkyl or alketh hydrocarbon side chains. The acidic monomer can comprise any acid functional group, for example sulfate, sulfonate, carboxylate, phosphonate, or phosphate or mixtures of acid groups. The acidic monomer can comprise, for example, a carboxylate, alternatively the acidic monomer is an acrylate, including acrylic acid and/or methacrylic acid. The acidic monomer comprises a polymerizable structure, e.g., vinyl functionality. Mixtures of acidic monomers, for example acrylic acid and methacrylic acid monomer mixtures, are useful.

The associative monomer can comprise a hydrophobic end group and a polymerizable component, e.g., vinyl, which can be attached. The hydrophobic end group can be attached to the polymerizable component, hence to the polymer chain, by different means but can be attached by an ether or ester or amide functionality, such as an alkyl acrylate or a vinyl alkanoate monomer. The hydrophobic end group can also be separated from the chain, for example, by an alkoxy ligand such as an alkyl ether. The associative monomer can be, for example, an alkyl ester, an alkyl (meth)acrylate, where (meth) acrylate is understood to mean either methyl acrylate or acrylate, or mixtures of the two.

The hydrophobic end group of the associative polymer can be incompatible with the aqueous phase of the composition and can associate with lathering surfactant hydrophobe components. Without intending to be limited by theory, it is believed that longer alkyl chains of structuring polymer hydrophobe end groups can increase incompatibility with the aqueous phase to enhance structure, whereas somewhat shorter alkyl chains having carbon numbers closely resembling lathering surfactant hydrophobes (e.g., 12 to 14 carbons) or multiples thereof (for bilayers, e.g.) can also be effective. An ideal range of hydrophobic end group carbon numbers combined with an optimal percentage of hydrophobic monomers expressed as a percentage of the polymer backbone can provide increased structure to the lathering, structured surfactant composition at low levels of polymer structurant.

The associative polymer can be Aqupec SER-300 made by Sumitomo Seika of Japan, which is Acrylates/C10-30 alkyl acrylate crosspolymer and comprises stearyl side chains with less than about 1% HM. Other preferred associative polymers can comprise stearyl, octyl, decyl and lauryl side chains. Preferred associative polymers are Aqupec SER-150 (acrylates/C10-30 alkyl acrylates crosspolymer) comprising about C18 (stearyl) side chains and about 0.4% HM, and Aqupec HV-701EDR which comprises about C8 (octyl) side chains and about 3.5% HM. In another example, the associative polymer can be Stabylen 30 manufactured by 3V Sigma S.p.A., which has branched isodecanoate hydrophobic associative side chains.

Other optional additives can be included in the cleaning phase, including for example an emulsifier (e.g., non-ionic emulsifier) and electrolytes. Suitable emulsifiers and electrolytes are described in U.S. patent application Ser. No. 13/157,665.

B. BENEFIT PHASE

As noted herein, personal care compositions can include a benefit phase. The benefit phase can be hydrophobic and/or anhydrous. The benefit phase can also be substantially free of or free of surfactant.

The benefit phase can also include a benefit agent. In particular, the benefit phase can comprise from about 0.1% to about 50%, by weight of the rinse-off personal care composition, of the benefit agent. The benefit phase can include, for example, from about 0.5% to about 20%, by weight of the rinse-off personal care composition, of the benefit agent. Examples of some suitable benefit agents include, for example, petrolatum, glyceryl monooleate, and mixtures thereof. Other suitable benefit agents are described in U.S. patent application Ser. No. 13/157,665.

The hydrophobic component can be, for example, a water-dispersible, non-volatile liquid. The water-dispersible, non-volatile liquid benefit agents can have a Vaughn Solubility Parameter (VSP) ranging from about 5 to about 14. Non-limiting examples of hydrophobic benefit materials having VSP values ranging from about 5 to about 14 include the following: Cyclomethicone (5.9), Squalene (6.0), Isopropyl Palmitate (7.8), Isopropyl Myristate (8.0), Castor Oil (8.9), Cholesterol (9.6), Butylene Glycol (13.2), soy bean oil, olive oil (7.87), mineral oil (7.1), and combinations thereof.

The hydrophobic benefit agents can have a viscosity less than 5000 cP measured at 25° C.

The benefit phase can typically comprise one or more benefit agents, as set forth above. Additional examples of benefit agents can include water insoluble or hydrophobic benefit agents.

Non-limiting examples of glycerides suitable for use as benefit agents herein can include castor oil, safflower oil, corn oil, walnut oil, peanut oil, olive oil, cod liver oil, almond oil, avocado oil, palm oil, sesame oil, soybean oil, vegetable oils, sunflower seed oil, vegetable oil derivatives, coconut oil and derivatized coconut oil, cottonseed oil and derivatized cottonseed oil, jojoba oil, cocoa butter, petrolatum, mineral oil, and combinations thereof.

Non-limiting examples of alkyl esters suitable for use as benefit agents herein can include isopropyl esters of fatty acids and long chain esters of long chain (i.e. C10-C24) fatty acids, e.g., cetyl ricinoleate, non-limiting examples of which can include isopropyl palmitate, isopropyl myristate, cetyl riconoleate, and stearyl riconoleate. Other example can include hexyl laurate, isohexyl laurate, myristyl myristate, isohexyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, acyl isononanoate lauryl lactate, myristyl lactate, cetyl lactate, and combinations thereof.

Non-limiting examples of alkenyl esters suitable for use as benefit agents herein can include oleyl myristate, oleyl stearate, oleyl oleate, and combinations thereof.

Non-limiting examples of polyglycerin fatty acid esters suitable for use as benefit agents herein can include decaglyceryl distearate, decaglyceryl diisostearate, decaglyceryl monomyriate, decaglyceryl monolaurate, hexaglyceryl monooleate, and combinations thereof.

Non-limiting examples of lanolin and lanolin derivatives suitable for use as benefit agents herein can include lanolin, lanolin oil, lanolin wax, lanolin alcohols, lanolin fatty acids, isopropyl lanolate, acetylated lanolin, acetylated lanolin alcohols, lanolin alcohol linoleate, lanolin alcohol riconoleate, and combinations thereof.

Non-limiting examples of silicone oils suitable for use as hydrophobic skin benefit agents herein can include dimethicone copolyol, dimethylpolysiloxane, diethylpolysiloxane, mixed C1-C30 alkyl polysiloxanes, phenyl dimethicone, dimethiconol, and combinations thereof. Nonlimiting examples of silicone oils useful herein are described in U.S. Pat. No. 5,011,681. Still other suitable hydrophobic skin benefit agents can include milk triglycerides (e.g., hydroxylated milk glyceride) and polyol fatty acid polyesters.

The benefit phase may also comprise a cationic hydrophobic polyethylene polymer. The cationic hydrophobic polyethylene polymer may be present from about 0.01% to about 5% by weight of the personal care composition. The cationic hydrophobic polyethylene polymer may be present from about 0.05% to about 2% by weight of the personal care composition. As another example, the cationic hydrophobic polyethylene polymer may be present from about 0.1% to about 1.5% by weight of the personal care composition.

An example of a suitable cationic hydrophobic polyethylene polymer includes an ethylene copolymer wherein the copolymer contains amino monomer. The amino monomer is, for example, amino acrylate. The polyethylene polymer can contain, for example, from about 1 to about 50% amino monomer by weight of the cationic hydrophobic polyethylene polymer. As another example, the polyethylene polymer can contain from about 5 to about 49% amino monomer by weight of the cationic hydrophobic polyethylene polymer. As an additional example, the polyethylene polymer contains from about 10 to about 48% amino monomer by weight of the cationic hydrophobic polyethylene polymer. As another example, the polyethylene polymer copolymer comprises poly(ethylene-co-DMAEMA). In an additional example, the polyethylene copolymer comprises dimethylaminoethyl methacrylate, diethylaminoethyl methacrylate, diethylaminoethyl acrylate, (4-hydroxyl-2,2,6,6-tetra-methylpiperridine) methacrylate, 2-Tert butyl amino ethyl methacrylate, or a combination thereof.

The cationic hydrophobic polyethylene polymer can have a viscosity at 120° C., for example, from about 50 to about 10,000 cps; from about 100 to about 8000 cps; or about 110 to about 5000 cps. The viscosity can be measured with a Dinamic Rotator Viscometer RS 600.

C. OPTIONAL INGREDIENTS

Additional optional ingredients can also be added to the personal care composition for treatment of the skin and/or hair, or to modify the aesthetics of the personal care composition as is the case with perfumes, colorants, dyes or the like. Optional materials useful in products herein can be categorized or described by their cosmetic and/or therapeutic benefit or their postulated mode of action or function. However, it can be understood that actives and other materials useful herein can, in some instances, provide more than one cosmetic and/or therapeutic benefit or function or operate via more than one mode of action. Therefore, classifications herein can be made for convenience and cannot be intended to limit an ingredient to particularly stated application or applications listed. A precise nature of these optional materials, and levels of incorporation thereof, will depend on the physical form of the composition and the nature of the cleansing operation for which it is to be used. Optional materials can usually be formulated at about 6% or less, about 5% or less, about 4% or less, about 3% or less, about 2% or less, about 1% or less, about 0.5% or less, about 0.25% or less, about 0.1% or less, about 0.01% or less, or about 0.005% or less of the rinse-off personal care composition.

To further improve stability under stressful conditions such as high temperature and vibration, densities of separate phases can be adjusted such that they can be substantially equal. To achieve this, low density microspheres can be added to one or more phases of the rinse-off personal care composition. Examples of rinse-off personal care compositions that comprise low density microspheres are described in a patent application published on May 13, 2004 under U.S. Patent Publication No. 2004/0092415A1 entitled "Striped Liquid Personal Cleansing Compositions Containing A Cleansing Phase and A Separate Phase with Improved Stability," filed on Oct. 31, 2003 by Focht, et al.

Other non-limiting optional ingredients that can be used in the personal care composition of the present invention can comprise an optional benefit component that can be selected from the group consisting of thickening agents; preservatives; antimicrobials; fragrances; chelators (e.g. such as those described in U.S. Pat. No. 5,487,884 issued to Bisset, et al.); sequestrants; vitamins (e.g. Retinol); vitamin derivatives (e.g. tocophenyl actetate, niacinamide, panthenol); sunscreens; desquamation actives (e.g. such as those described in U.S. Pat. Nos. 5,681,852 and 5,652,228 issued to Bisset); anti-wrinkle/anti-atrophy actives (e.g. N-acetyl derivatives, thiols, hydroxyl acids, phenol); anti-oxidants (e.g. ascorbic acid derivatives, tocophenol) skin soothing agents/skin healing agents (e.g. panthenoic acid derivatives, aloe vera, allantoin); skin lightening agents (e.g. kojic acid, arbutin, ascorbic acid derivatives) skin tanning agents (e.g. dihydroxyacteone); anti-acne medicaments; essential oils; sensates; pigments; colorants; pearlescent agents; interference pigments (e.g such as those disclosed in U.S. Pat. No. 6,395,691 issued to Liang Sheng Tsaur, U.S. Pat. No. 6,645,511 issued to Aronson, et al., U.S. Pat. No. 6,759,376 issued to Zhang, et al, U.S. Pat. No. 6,780,826 issued to Zhang, et al.) particles (e.g. talc, kolin, mica, smectite clay, cellulose powder, polysiloxane, silicas, carbonates, titanium dioxide, polyethylene beads) hydrophobically modified non-platelet particles (e.g. hydrophobically modified titanium dioxide and other materials described in a commonly owned, patent application published on Aug. 17, 2006 under Publication No. 2006/0182699A, entitled "Personal Care Compositions Containing Hydrophobically Modified Non-platelet particle filed on Feb. 15, 2005 by Taylor, et al.) and mixtures thereof. The multiphase personal care composition can comprise from about 0.1% to about 4%, by weight of the rinse-off personal care composition, of hydrophobically modified titanium dioxide. Other such suitable examples of such skin actives are described in U.S. patent application Ser. No. 13/157,665.

Other optional ingredients can be most typically those materials approved for use in cosmetics and that are described in the CTFA Cosmetic Ingredient Handbook, Second Edition, The Cosmetic, Toiletries, and Fragrance Association, Inc. 1988, 1992.

D. EXEMPLARY COMBINATIONS

As one example, a personal care composition comprises a cleansing phase comprising a water soluble cationic polymer and a surfactant; and a benefit phase comprising a hydrophobic benefit agent and a cationic hydrophobic polyethylene polymer.

As another example, a personal care composition comprises a cleansing phase comprising an anionic surfactant and a water soluble cationic polymer; and a benefit phase comprising a hydrophobic benefit agent selected from the group consisting of petrolatum, soy bean oil, sefose, and combinations thereof, and a cationic hydrophobic polyethylene polymer.

In an additional example, a personal care composition comprises a cleansing phase comprising an anionic surfactant, a cosurfactant, a water soluble cationic polymer, an associative polymer, and an electrolyte; and a benefit phase comprising a benefit agent comprising an ethylene copolymer. In a further example, the ethylene copolymer comprises poly(ethylene-co-DMAEMA).

In another example, a personal care composition comprises a cleansing phase comprising sodium tridecyl ether sulfate and guar hydroxypropyltrimonium chloride; and a benefit phase comprising soy bean oil and poly(ethylene-co-DMAEMA).

In the above exemplary combinations, the pH can range from 4.5 to about 9.

E. METHODS

In addition to the compositions above, inventive methods are also present. For example, a method for increasing benefit agent deposition to skin and/or hair in a personal cleansing composition includes combining a surfactant, a water soluble cationic polymer, a benefit agent, and a cationic hydrophobic polyethylene polymer to form a person care composition. As an example, the surfactant and water soluble cationic polymer are in a cleansing phase while the benefit agent and cationic hydrophobic polyethylene polymer are in a benefit phase. In a further example, the personal cleansing composition is applied to skin of a user and rinsed off. As an example, the cationic hydrophobic polyethylene polymer comprises poly (ethylene-co-DMAEMA).

A method of increasing coacervate rheology comprising combining a surfactant, a water soluble cationic polymer, a benefit agent, and a cationic hydrophobic polyethylene polymer to form a personal care composition and then diluting the personal care composition with water. In one example, the surfactant and water soluble cationic polymer are in a cleansing phase while the benefit agent and cationic hydrophobic polyethylene polymer are in a benefit phase. In a further example, the personal cleansing composition is applied to skin of a user and rinsed off. In another example, the cationic hydrophobic polyethylene polymer comprises poly(ethylene-co-DMAEMA).

A method of increasing encapsulation of a benefit agent in a coacervate comprising combining a surfactant, a water soluble cationic polymer, a benefit agent, and a cationic hydrophobic polyethylene polymer to form a personal care composition and then diluting the personal care composition with water. In one example, the surfactant and water soluble cationic polymer are in a cleansing phase while the benefit agent and cationic hydrophobic polyethylene polymer are in a benefit phase. In a further example, the personal cleansing composition is applied to skin of a user and rinsed off. In another example, the cationic hydrophobic polyethylene polymer comprises poly(ethylene-co-DMAEMA).

For simplicity, only a minimal amount of compositional ingredients and variants are discussed here. The above disclosure relating to the compositions and ingredients are equally applicable here as well.

F. EXAMPLE

Example 1

| Rinse off Composition | Comparative | | | | | Inventive | | | | |
|---|---|---|---|---|---|---|---|---|---|---|
| | Ex. A | Ex. B | Ex. C | Ex. D | Ex. E | Ex. F | Ex. G | Ex. H | Ex. I | Ex. J |
| Cleansing phase, % | | | | | | | | | | |
| Distilled Water | Q.S. | Q.S. | Q.S. | Q.S. | Q.S. | Q.S. | Q.S. | Q.S. | Q.S. | Q.S. |
| Sodium Tridecyl Ether Sulfate | 12.6 | 12.6 | 12.6 | 12.6 | 12.6 | 12.6 | 12.6 | 12.6 | 12.6 | 12.6 |
| Laurylamidopropyl Betaine | 7.67 | 7.67 | 7.67 | 7.67 | 7.67 | 7.67 | 7.67 | 7.67 | 7.67 | 7.67 |
| Sodium Chloride | 4.75 | 4.75 | 4.75 | 4.75 | 4.75 | 4.75 | 4.75 | 4.75 | 4.75 | 4.75 |
| Iconol TDA3-Ethoxylated Tridecyl Alcohol | 1.40 | 1.40 | 1.40 | 1.40 | 1.40 | 1.40 | 1.40 | 1.40 | 1.40 | 1.40 |
| N-Hance CG17 Cationic Guar | — | — | — | — | 0.42 | 0.42 | 0.42 | 0.42 | — | — |
| polyquaternium 76 (AM:Triquat 95:5) | — | — | — | — | — | — | — | — | 0.42 | — |
| PAMMAPTAC (AM:MAPTAC 88:12) | — | — | — | — | — | — | — | — | — | 0.42 |
| Preservative 1 | 0.28 | 0.28 | 0.28 | 0.28 | 0.28 | 0.28 | 0.28 | 0.28 | 0.28 | 0.28 |
| Preservative 2 | 0.037 | 0.037 | 0.037 | 0.037 | 0.037 | 0.037 | 0.037 | 0.037 | 0.037 | 0.037 |
| Associative Polymer | 0.15 | 0.15 | 0.15 | 0.15 | 0.15 | 0.15 | 0.15 | 0.15 | 0.15 | 0.15 |
| Sequestering agent | 0.15 | 0.15 | 0.15 | 0.15 | 0.15 | 0.15 | 0.15 | 0.15 | 0.15 | 0.15 |
| Oxidizer (50% solution) | 0.07 | 0.07 | 0.07 | 0.07 | 0.07 | 0.07 | 0.07 | 0.07 | 0.07 | 0.07 |
| Benefit phase, % | | | | | | | | | | |
| Hydrophobic benefit agent (soy bean oil) | 10.0 | 9.0 | 9.0 | 9.0 | 10.0 | 9.0 | 9.0 | 9.0 | 9.0 | 9.0 |
| Ethylene-DMAEMA copolymer (Polymer 6) | — | 1.0 | — | — | — | 1.0 | — | — | — | — |
| Ethylene-DMAEMA copolymer (Polymer 4) | — | — | 1.0 | — | — | — | 1.0 | — | — | — |
| Ethylene-DMAEMA copolymer (Polymer 1) | — | — | — | 1.0 | — | — | — | 1.0 | 1.0 | 1.0 |
| Product pH | 5.37 | 7.79 | 7.49 | 7.85 | 5.54 | 7.87 | 7.26 | 7.70 | 7.35 | 7.50 |
| In vitro Soybean oil deposition ($\mu g/cm^2$) | 2.0 | 2.7 | 2.2 | 2.6 | 16 | 55 | 177 | 392 | 66 | 379 |

The cleansing phase of both the inventive and comparative formulations are prepared by adding water in a mixing vessel. Then the following ingredients are added with continuously mixing: sodium chloride, water soluble cationic polymer if applicable (e.g. N-hance CG-17 cationic guar), laurylamidopropyl betaine, sodium tridecyl sulfate, ethoxylated tridecyl alcohol, sequestering agent, and associative polymer. The pH is then adjusted by adding oxidizer (50% solution) as needed to attain a pH=5.7±0.2. Then the preservatives are added and the phase mixed until homogeneous.

The benefit phase, if only soy bean oil, is added to the cleansing phase. The mixture is mixed at 2000 rpm for 1 minute on a SpeedMixer™ (Model DAC, 400FV available from FleckTeck, Inc USA). If the benefit phase comprises a hydrophobic cationic polyethylene polymer (Polymer 6, 4, or 1) in addition to the soybean oil, then the polymers are heated to a few degrees (3-5° C.) above their glass transition temperature (Tg) in the soy bean oil prior to the addition of the benefit phase to the cleansing phase. The two components are mixed with any standard mixing techniques until the polymer is mixed into the soybean oil. While warm the benefit phase is added to the cleansing phase followed by speed mixing described above. To avoid the formation of large chunks of the benefit phase in the cleansing phase, the cleansing phase may be warmed to a similar temperature as the benefit phase before mixing.

G. TEST PROTOCOL

Fastmice

In-Vitro Deposition Evaluation Method:

The In-vitro Deposition Evaluation Method measures the deposition of benefit agents on a skin mimic. The method compares the quantity of benefit agent of the skin mimic surface before and after cleansing in an automated cleansing unit, such as the automated cleansing unit described in co-pending and co-assigned Multiphase Personal Care Composition With Enhanced Deposition, U.S. application Ser. No. 12/510,880 (filed Jul. 28, 2009) and In-Vitro Deposition Evaluation Method for Identifying Personal Care Compositions Which Provide Improved Deposition of Benefit Agents, U.S. application Ser. No. 12/511,034 (filed Jul. 28, 2009).

The In-vitro Deposition Evaluation Method uses two 12-well plates (hereinafter referred to as "plates"). Suitable 12-well plates are commercially available from Greiner bio-one. For example, the Cellstar® 12 well suspension culture plate has 3 rows and 4 columns with a well volume of about 6.2 mL. The Cellstar® 12 well suspension culture plate comprises the approximate dimensions of 19 mm in height, 127 mm in length and 85 mm in width. The Cellstar® 12 well suspension culture plate has a well diameter of 23 mm, a well depth of 15 and a well to well spacing of 2 mm A Cellstar® 12 well suspension culture plate is provided for containing the samples comprising the personal care composition in the Examples above.

The In-vitro Deposition Evaluation Method uses approximately 120 g of bodies for two plates. Five grams of bodies carefully loaded into each of the 12 wells of the two plates to ensure the same quantity is loaded into each well. Each body is a spherical stainless steel bearing that is approximately 2 mm in circumference. Each body comprises ferrometallic material. Suitable bodies are those available from WLB Antriebeselemente Gmbh, Scarrastrasse 12, D-68307 Mannheim, Germany.

The personal care compositions are prepared according to the description in the Example Section above. After the examples of the personal care compositions are prepared, control and test samples are prepared by determining the dilution ratio and dispensing both the personal care composition and distilled water into the wells of the microplate and allow the samples to mix while being exposed to the automated washing process. The dilution ratio used in this application is one part of composition and twenty nine parts of water (1:29). A pre-calibrated positive displacement pipette is used to dispense 66.7 µL of composition on to the bodies in each well, followed by dispensing 1933.3 µL of distilled water into each well. The control samples and test samples are dispensed in the specified wells of the plate, all within a 20 minute time frame. Each composition is placed in 6 different well, 3 of which are in plate 1 and the other 3 well are in plate 2. A test control composition containing the benefit agent should be used in every test to ensure consistency among tests.

The skin mimic used in the In-vitro Deposition Evaluation Method is comprised of a molded bicomponent polyurethane substrate. The skin mimic is textured on one side with a pattern that resembles the texture of human skin. The textured side of the skin mimic is coated with 1,1,1-trimethyl-1-pentene that is plasma deposited. The skin mimic surface has a total surface energy of $32±1.0$ $(mJ/m^2)$ and a contact angle in water of $100°±2.0$. Suitable skin mimic surface materials are described in co-pending and co-assigned Coated Substrate with Properties of Keratinous Tissue, U.S Patent Pub. No. 20070128255A1 (filed Aug. 11, 2006) (published Jun. 7, 2007) and Methods of Use of Substrate Having Properties of Keratinous Tissue, U.S Patent Pub. No. 20070288186A1 (filed Feb. 5, 2007) (published Dec. 13, 2007).

After all of the wells of the plate are filled with the samples and the pieces of skin are made and coated, the skin mimic is prepared for the In-vitro Deposition Evaluation Method. Two pieces of skin mimic are prepared by cutting the skin mimic to fit on top of all 12 openings of the wells of the plate while wearing gloves. The two pieces of skin mimic pieces are numbered "1" and "2".

Next, the pieces of skin mimics are arranged over the openings of the wells of the microplates. The pieces of skin mimic surface material are transferred to cover the openings of the wells of the each of the plates to ensure that the textured and treated region of the skin mimic is facing the openings of the wells of the plate. A lid is placed over each piece of the skin mimic and the associated plate to form a lidded plate.

The lidded plates are placed into plate holders of an automated cleansing unit, or, a device used in the in-vitro Deposition Evaluation Method of the present invention. The automated cleansing unit comprises a horizontal base comprising four microplate holders. The horizontal base is made of rectangle of aluminum comprising the following approximate dimensions of ⅜ inch in height, fourteen inches in width and twenty seven inches in length. The automated cleansing unit further comprises two vertical supports comprised of aluminum with the approximate dimensions of one inch by two inches by ten and ¾ of an inch in height. The vertical supports are attached to a horizontal support comprising a rodless air slide. The horizontal support comprising a rodless air slide comprises the approximately dimension of a ½ inch by two inches by twenty six and ½ inches in height. Suitable rodless air slides comprise a one inch bore and eleven inch stroke and have associated end lugs and mount brackets, which are commercially available from McMaster-Carr. The rodless air slide can be double acting and comprises a carriage that is connected to an internal piston and two compressed air ports.

The automated cleansing unit comprises two magnetic arms. The horizontal support comprising a rodless air slide is the structure upon which the two magnetic arms are mounted. The magnetic arms are mounted to the rodless air slide such that the magnetic arms move back and forth along the length of the double acting rodless air slide by the force of compressed air. Each of the magnetic arms are comprised of aluminum and have the approximate dimensions of one inch by two inches by fourteen inches in length and have a "T" shape channel that houses seven neodymium iron boron magnets (not shown). Each of the neodymium iron boron magnets has the approximate dimensions of two inches in length, one inch in width and half or an inch in height. Each of the neodymium iron boron magnets comprises a magnetic strength of 12200 Gauss, available from Edmund Scientifics. The magnetic arms are configured at a height of about 2.75 cm above the microplate holder with the caveat that the magnets maintain their function to attract and move the bodies comprised within the wells of the microplate. The magnetic arms move back and forth along the length of the rodless air slide by the force of compressed air at a speed of approximately 6 back and forth sweeps over the length of the rodless air slide over a 10 second time period.

The magnetic arms can be configured with four microplate holders. Each of the microplate holders comprise a clamping plate and four pistons attached to a pneumatic control unit. When actuated, the pistons for the pneumatic control unit hold the plates in the four plate holders at a pressure of about 90 psi. Prior to placing the lidded plates into the plate holders of automated cleansing unit, the pneumatic control unit is turned on.

The automated cleansing unit can comprise a pneumatic control unit. The top view shows components of the pneumatic control unit which can be connected to the rodless air slide, the piston and clamping plates. The pneumatic control unit can be used to apply compressed air to the automated cleansing unit, which imparts a force by converting the potential energy of compressed air into kinetic energy. The pneumatic control unit comprises a solenoid air control valve, a distribution manifold outlet, a compressed air control valve, a compressed air flow regulator, an alternating output binary valve, a two-hand safety pneumatic control valve, a compressed air control valve and various connectors that provide pressurized air to the automated cleansing unit from an external air source. The air control valve, air flow regulators, alternating a binary valves, a two-hand safety pneumatic control valve are positioned upstream of a solenoid air control valve. A suitable solenoid air control valve can be described as a double air style valve with a 10 psi to 120 operating pressure. Suitable compressed air flow regulators can operate, for example, in the pressure range of 14 psi to 116 psi. Suitable air control valve alternating output binary valves 40 can operate, for example, in a 35 psi to 100 psi range. All of the components of the pneumatic control unit are available from McMaster-Carr®.

The lidded plates are placed into the plate holders and pneumatic control unit is actuated such that the lidded plates are held under 90 psi of pressure. The magnetic arms are actuated on and arms moves over the lidded microplates at a height of 2.65 cm above the plate holders. The magnetic arms of the automated cleansing unit, sweep back and forth over the plate holders for 5 minutes, at a speed of 6 sweeps per every 10 seconds. After 5 minutes of the automated cleansing process, the lidded plates are removed from the plate holders and are disassembled.

After the automated washing process, two large 4000 ml beakers of 20° C. to 25° C. water are filled. The first piece of skin mimic is removed from the first plate and submerged in the tap water within the first beaker five times. The second piece of skin mimic is removed from the second microplate and submerged within the second beaker five times. The completeness of rinsing step is judged visually by the lack of foam on the skin mimic and presence of defined circles of deposited material on the skin mimic. Both piece of skin mimic are blotted gently with paper towels and fumed in a drying hood for at least 3 hours each.

The cut-out pieces of treated skin mimic are then extracted with a solvent and the extract is analyzed and quantified by gas chromatography.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for increasing benefit agent deposition to skin in a personal cleansing multi-phase composition comprising a cleansing phase and a benefit phase, wherein the surfactant and water soluble cationic polymer are in a cleansing phase, ethylene-dimethylaminoethyl methacrylate copolymer and benefit agent are in the benefit phase.

2. The method of claim 1, wherein the personal cleansing multi-phase composition comprises a pH of about 4.5 to about 9.

3. The method of claim 1, further comprising applying the personal cleansing multi-phase composition to the skin of a user and rinsing the personal cleansing multi-phase composition from the skin.

* * * * *